(12) United States Patent
Goldstein et al.

(10) Patent No.: US 6,640,199 B1
(45) Date of Patent: Oct. 28, 2003

(54) SYSTEM AND METHOD FOR OPTICALLY DETERMINING PROPERTIES OF HOT FLUIDS FROM THE SPECTRAL STRUCTURE OF EMITTED RADIATION

(75) Inventors: Neil Goldstein, Belmont, MA (US); John Gruninger, Boston, MA (US); Fritz Bien, Concord, MA (US); Jamine Lee, Burlington, MA (US)

(73) Assignee: Spectral Sciences, Inc., Burlington, MA (US)

( * ) Notice: Subject to any disclaimer, the term of this patent is extended or adjusted under 35 U.S.C. 154(b) by 0 days.

(21) Appl. No.: 09/999,807

(22) Filed: Oct. 24, 2001

(51) Int. Cl.[7] .............................................. G01K 11/30
(52) U.S. Cl. ........................ 702/134; 702/135; 702/28
(58) Field of Search ................................ 702/134, 135, 702/28

(56) References Cited

U.S. PATENT DOCUMENTS 6,370,486 B1 * 4/2002 Sivathanu .................... 702/135

* cited by examiner

*Primary Examiner*—John Barlow
*Assistant Examiner*—Anthony Dougherty
(74) *Attorney, Agent, or Firm*—Brian M. Dingman, Esq.; Mirick, O'Connell, DeMalli & Lougee, LLP (57) ABSTRACT

A system and method for remotely determining at least one of the temperature of, and the relative concentrations of species making up, a hot fluid, based on the spectral structure of radiation emitted from the fluid. Thermal radiation over a field of view including the hot fluid is collected. At least a portion of the emission spectrum from the collected radiation is resolved. The resolved emission spectrum is resolved into spectra that are characteristic of specific emitting species and emitter temperatures. The temperature of, and the relative concentrations of species making up, the hot fluid, are determined from the relative amounts of at least two resolved spectra.

50 Claims, 10 Drawing Sheets

SYSTEM AND METHOD FOR OPTICALLY DETERMINING PROPERTIES OF HOT FLUIDS FROM THE SPECTRAL STRUCTURE OF EMITTED RADIATION

GOVERNMENT RIGHTS

This invention was made with Government support under Contract No. F3361-01-C-2117 awarded by the Department of the Air Force, AFRL/PRTC. The Government has certain rights in this invention.

FIELD OF THE INVENTION

This invention relates to a system and method for determining the temperature and species make-up of a hot fluid, based on emitted thermal radiation.

BACKGROUND OF THE INVENTION

Real-time temperature and chemical sensing methods are needed to monitor and control the efficiency, performance, and safety of combustion in systems such as turbine engines and industrial boilers. Strict control of temperature and exhaust composition is required to limit damage to sensitive components, control emissions, and increase output power and efficiency. Attempts to control combustion and achieve temperature uniformity have been hampered by the lack of sensors to monitor and spatially resolve the burner temperatures. In addition, there is a requirement to measure the chemical composition of the hot fluid to determine the extent to which combustion is complete, as un-combusted species may release additional heat when mixed with air.

For gas turbine engines, a critical limitation is the requirement that the combustor exit temperature stay below the damage threshold of the turbine blades. Accurate measurements of the spatial temperature distribution or pattern factor are required for experimental validation of burner capabilities and for use in active combustion control technologies. However, these measurements are rendered difficult by many factors, including the extreme conditions of the combustor environment (temperatures to 2500 K or 4000 F and pressures to 40 atmospheres), the inaccessibility of the measurement zone, and the possible presence of obscuring, surface-fouling soot.

Efforts underway to actively control the combustion process in gas turbines are severally limited by the lack of sensors capable of monitoring the effects of control actuators. In contrast to internal combustion engines that have real-time closed-loop control of fuel flow, current turbine engine technology depends on open-loop control of fuel air mixture, which results in large variations in conditions and efficiency across burners and among burners in the same engine.

Currently, thermocouples and pyrometers are used to infer the temperature of the hot fluid. Thermocouples are very useful at lower temperatures, but have performance, lifetime, and calibration issues at moderate temperatures (1,000–2000 K) and cannot be used at all at higher temperatures. Pyrometers are often used to optically measure the temperature of a hard surface within the boiler or turbine engine. Fluid temperature is then inferred from the surface temperature. Other optical techniques infer the combustion gas temperature from the intensity of the emitted radiation in one or more spectral regions characteristic of chemical intermediates in the combustion process. More sophisticated spectroscopic techniques such as tunable diode laser (TDL) absorption spectroscopy, laser-induced-fluorescence (LIF), coherent anti-Stokes Raman spectroscopy (CARS), and Fourier transform infrared (FTIR) spectroscopy have been used to determine temperature and composition in research applications. Such methods often have the disadvantage of requiring optical access from multiple viewpoints, critical alignment, and expert technical personnel to gather and interpret the data.

SUMMARY OF THE INVENTION

The invention offers significant advantages over these prior-art techniques. The invention solves these critical needs in one embodiment with a robust, flight-worthy sensor that can provide a variety of signals suitable for burner control, including temperature, fuel/air mixing ratio, and spatial distributions of these quantities.

The invention employs a passive measurement requiring a single port for optical access, has no critical alignment requirements, and is independent of pressure. It can be used over a large temperature range, and with no upper limit. It provides an accurate direct measurement of the temperature and/or relative concentrations of several molecular and particulate species within the hot fluid. Unlike methods based on inference, the measured component temperatures are independent of the details of the hot fluid source, and thus can be applied to any hot fluid containing those components. Spatially resolved measurements can be made using multiple views of the hot region. When compared to other optical methods, the invention is relatively simple, and the associated hardware is inherently less expensive, more reliable, and, ultimately, more readily adaptable as a flight-weight measurement system.

The preferred embodiment of the invention involves the use of passive optic probes, and a compact, flight-weight spectrograph to collect the bright structured emission features observable in the hot fluid flow path of a turbine engine. A simple optic probe is placed near the hot fluid, with a view of the hot region. The probe might have a diameter of several millimeters and consist of a collimating lens and an optical fiber, or a coherent fiber bundle. The fiber probe collects light emitted along a line-of-sight and directs it to the input of a spectrograph contained in a remote optical readout unit. The spectrograph disperses the light, and the dispersed light is recorded by an array detector, digitized, and processed to yield an emission spectrum. The visible and/or infrared emission spectra observed along one or more fields-of-view are continuously recorded at intervals of a fraction of a second and a spectral resolution of order $1/100^{th}$ of the collected spectral interval. The recorded spectra are decomposed into component spectra of various emitting species in the hot fluid, such as water, soot, oxygen, carbon monoxide, and/or carbon dioxide. The temperature of each emitter can be determined from the shape of the spectra on a sub-second time scale, using spectral discrimination techniques. In contrast to pyrometric measurements based on the intensity of the emitted radiation or the relative intensity in multiple bands, this invention can determine the temperature based solely on the characteristic shape of a single species spectrum, which is independent of the amount of each species in the hot fluid. The spectra have sufficient information content to uniquely determine the temperature to better than 10° C., and the relative concentration of the various gaseous emitters, and of soot, if present.

Spatially resolved measurements can be made using a variety of probe configurations. A probe may use a single fiber or a free space optical transfer system to interrogate a single field-of-view. Alternatively, a probe can use multiple optical fibers to define multiple fields-of-view terminating at the probe. The probe can be set back from the measurement region to define several near parallel fields of view though the hot region.

In an alternative embodiment, multiple fiber probes can be used to make simultaneous measurements of several views of the combustor. In a turbine engine, the circumferential pattern. of the temperature and/or composition can be determined using radial-viewing probes arrayed about the arc defined by the engine annulus.

In yet another alternative embodiment, multiple-fiber probes with overlapping views of the same region can be used to define volume elements within the flow. Spatial reconstruction techniques, such as tomography, can then be used to resolve the emitted radiation from each volume element, and determine the temperature and/or species concentration of each volume element.

The invention is suitable for collecting diagnostic information in engine tests, or can be used as a sensor as a part of an engine monitoring system, or an engine closed-loop control system. Data can be collected, processed, and output on a sub-second time scale. One or more output signals maybe generated for part of the control system. These include temperature; temperature spatial distribution; concentrations of soot, water, $O_2$, and other component gases; spatial distribution of components; and mixing ratios of components, such as the water/oxygen ratio. The water/oxygen ratio is a direct indicator of the completeness of combustion, and can serve as a direct control signal for adjusting the fuel/air mixture in the combustor, in much the same way as an oxygen sensor is used to control an internal combustion engine.

The sensor may be placed in any desired and possible location in the combustion system to obtain information for diagnostic and control purposes. For example, the probe may be to positioned to measure the temperature or composition of the gas at the exit of the combustor and just prior to the inlet of the turbine, to monitor the temperature and latent heat content of the hot fluid to assure the safety of the turbine blade. Spatially resolved measurements may be made at this location to monitor and control the temperature distribution in the hot flow. Alternatively, the sensors may be placed upstream of the combustion zone with a view through the entire combustion flow field. This will allow the measurement of the maximum temperature, temperature distribution, and/or stoichiometry in the combusting gas, for use in controlling the fuel/air mixture.

BRIEF DESCRIPTION OF THE DRAWINGS

Other objects, features and advantages will occur to those skilled in the art from the following description of the preferred embodiment, and the accompanying drawings, in which.

DETAILED DESCRIPTION OF THE PREFERRED EMBODIMENTS

Figure 1A:
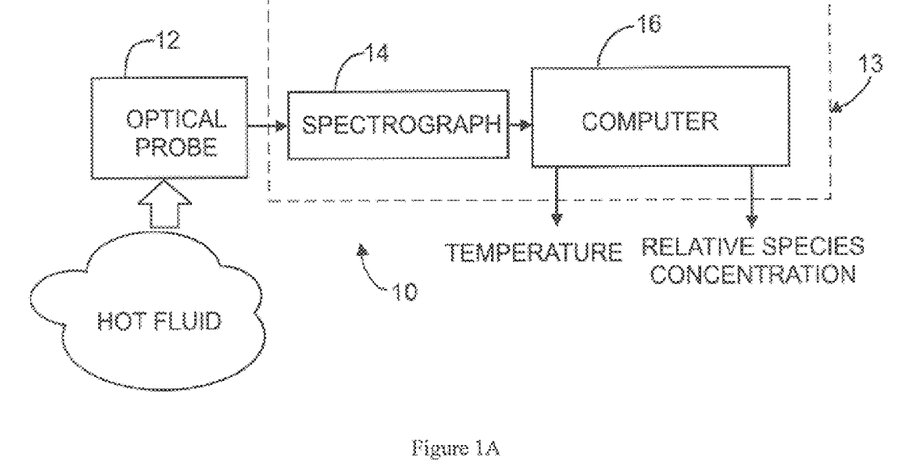
FIG. 1A is a schematic diagram of a system of this invention, that is also useful to accomplish the method of this invention.

In a preferred embodiment shown in FIG. 1, inventive system 10 comprises two compact modules; a probe module 12 and an optical readout (spectrograph) module 13, connected by optical fibers, or other means of transmitting the collected light. Light from the hot fluid within the field of view is collected by optical probe 12, is transmitted to spectrograph 14, dispersed by spectrograph 14, and detected by the spectrograph's CCD or CMOS array detector. The signal detected by the array detector is digitized and sent to data processing module 16.

Optical probe 12 preferably consists of a housing that holds a lens and optical fibers in a pre-determined position so that the fibers will collect light over a defined field of view. The preferred field of view is cylindrical or cone shaped, and of the order of 2–20 mm in diameter. For use in a combustor, probe 12 may also have provision for attaching the probe to the superstructure of the combustor apparatus, and keeping the optical components within their safe operating temperature. Typical optical components might include a sapphire lens or window that can withstand exposure to hot gases at temperatures exceeding 2000 K, and polyimide-clad silica—silica optical fibers that have an upper operating temperature of about 650 K. The probe may use passive or active means to keep the fibers below this upper operating temperature. Passive means may include mounting the probe in a cool region, or keeping the probe in good thermal contact with a low temperature structural element. Active means might include cooling the probe with a flowing fluid such as water, fuel, or uncombusted air. The system may also include a flow of air or cooling gas over the probe to cool the components and keep the optical elements free of soot buildup.

The optical readout consists of spectrograph 14 with an array detector, and data processing module 16. In some applications, an additional white light source may be included for automatic calibration of the readout response. In one preferred embodiment, the spectrograph would be a multi-channel spectrograph with multiple fiber inputs. Each fiber input would correspond to a unique field of view through the hot fluid. The fiber inputs would be aligned along the length of the input slit. A two-dimensional array detector at the exit of the spectrograph would be used to record the dispersed image of the various input fibers; one dimension of the array would correspond to the wavelength of the dispersed light, and the other dimension corresponds to the location of each input fiber. Alternatively, a single-channel spectrograph with a one-dimensional array detector can be used to record the spectrum of each field-of-view. Alternatively, other means, such as a prism, interferometer, or tunable filter may be used to record the continuous spectrum of the collected radiation.

The properties of the spectrograph and array detectors may be adjusted to meet the requirements of a particular measurement. In general, shorter wavelengths are used to monitor higher temperatures, and longer wavelengths are used to monitor lower temperatures. Wavelength ranges are also dictated by the characteristic emission wavelengths of the components to be measured.

Figure 1B:
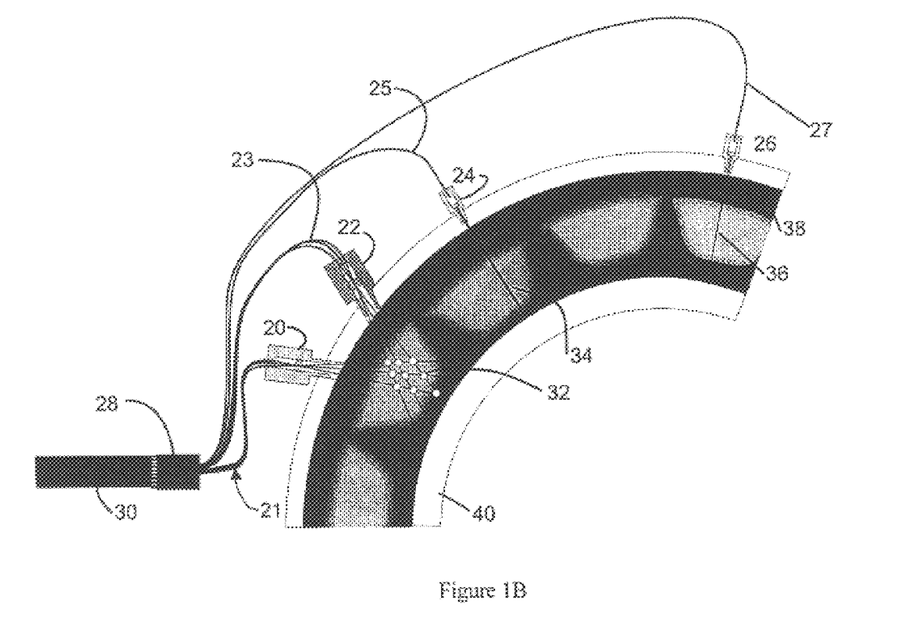
FIG. 1B is a schematic drawing of different possible arrangements of probes for collecting thermal radiation, for this invention.

In one preferred embodiment for monitoring temperatures inside turbine combustor engines, emission in the visible and near-infrared portion of the spectrum is used to monitor the temperature of water and soot, and the concentrations of water, soot and $O_2$. A schematic illustration is shown in FIG. 1B, for probes aligned along a portion 40 of the annular combustion zone 38 of a turbine engine. The radiation can be detected with silicon-based array detectors, such as CCD or CMOS detector arrays in the range of 700–1200 nm. Other embodiments might use other detectors, such as GaAs-based detectors operating from 800–1700 nm, or infrared detectors operating in the 1.5–13 micron range.

Measurements can be made using a variety of probe configurations illustrated in the figure. A probe may use a single fiber, such as probes 24 and 26 with single fibers 25 and 27, respectively, or a free space optical transfer system to interrogate a single field-of-view, 34 and 36, respectively. Alternatively, a probe can use multiple optical fibers to define multiple fields-of-view terminating at the probe. Probes 20 and 22 are of this configuration, with multiple fiber bundles 21 and 23, respectively, and the fields of view indicated by the solid lines leading into interrogated area 32. Fiber-optic junction box 28 is used to direct all of the collected radiation a through fiber bundle 30 to the spectrograph.

The probe can be set back from the measurement region to define several overlapping or near parallel fields of view though the hot region, to accomplish a desired objective. In an alternative embodiment, multiple fiber probes can be used to make simultaneous measurements of several views of the combustor. In a turbine engine, the circumferential pattern of the temperature and/or composition can be determined using radial-viewing probes arrayed about the arc 38 defined by the engine annulus 40.

In yet another alternative embodiment, multiple-fiber probes 20 and 22 with overlapping views of the same region 32 can be used to define volume elements within the flow, indicated by the small circles where the field-of-view lines cross. Spatial reconstruction techniques, such as tomography, can then be used to resolve the emitted radiation from each volume element, and determine the temperature and/or species concentration of each volume element.

The optical readout uses well-established spectrograph and array detector technology that allow it to meet the requirements of both in-flight and ground-based sensors systems. For in-flight systems, the optical system must be robust, lightweight, and reliable. The multi-channel spectrograph and array detector technology can meet these requirements. Commercial versions weighing less than one pound and with no moving parts are readily available. For ground based applications, low cost arid ease-of use are very important. Low cost multi-channel spectrographs are readily available. The use of low-cost silicon array detectors can be a critical advantage for cost-sensitive applications, as many standard silicon array detectors made for photographic and machine vision applications offer very high performance at a very low cost. The optical readout device is easy to use. After installation, the optical readout operates continuously, with no required maintenance or calibration, and requires no consumables.

Figure 2A:
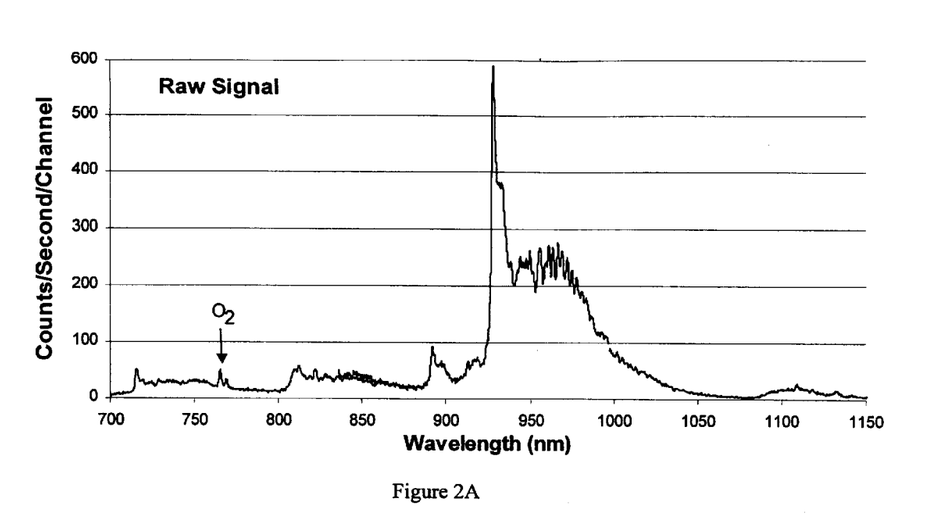
FIG. 2A is an example of a typical silicon detector signal measured in a flame with an approximate temperature of 1950K (3000 F)
Figure 2B:
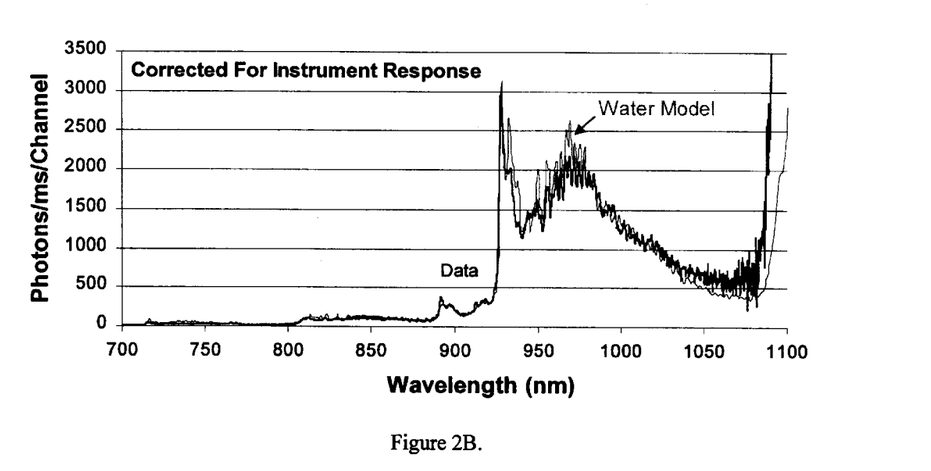
FIG. 2B shows the same data as that of FIG. 2A, corrected for the instrument response function.

FIG. 2A shows a typical silicon detector signal measured in a flame with an approximate temperature of 1950 K (3000 F). Three overlapping spectra were collected at center wavelengths of 640 nm, 915 nm, and 1075 nm respectively. The doublet feature at 767 nm is due to $O_2$. The rest of the spectrum arises from hot water. Additional radical emissions from CN, $C_2$, and CO+O recombination reactions were observed at shorter wavelengths. The spectral survey shows several water band systems ranging from the (301) band near 720 nm to the (210) band near 1150 nm. With the exception of the (201) band near 950 nm, all of these bands have similar signal strengths. The bands at longer wavelength are stronger than those at shorter wavelength, but the detector is less sensitive at longer wavelengths. FIG. 2B shows the same data corrected for the instrument response function. Also shown for comparison is a theoretical water spectrum.

Figure 3A:
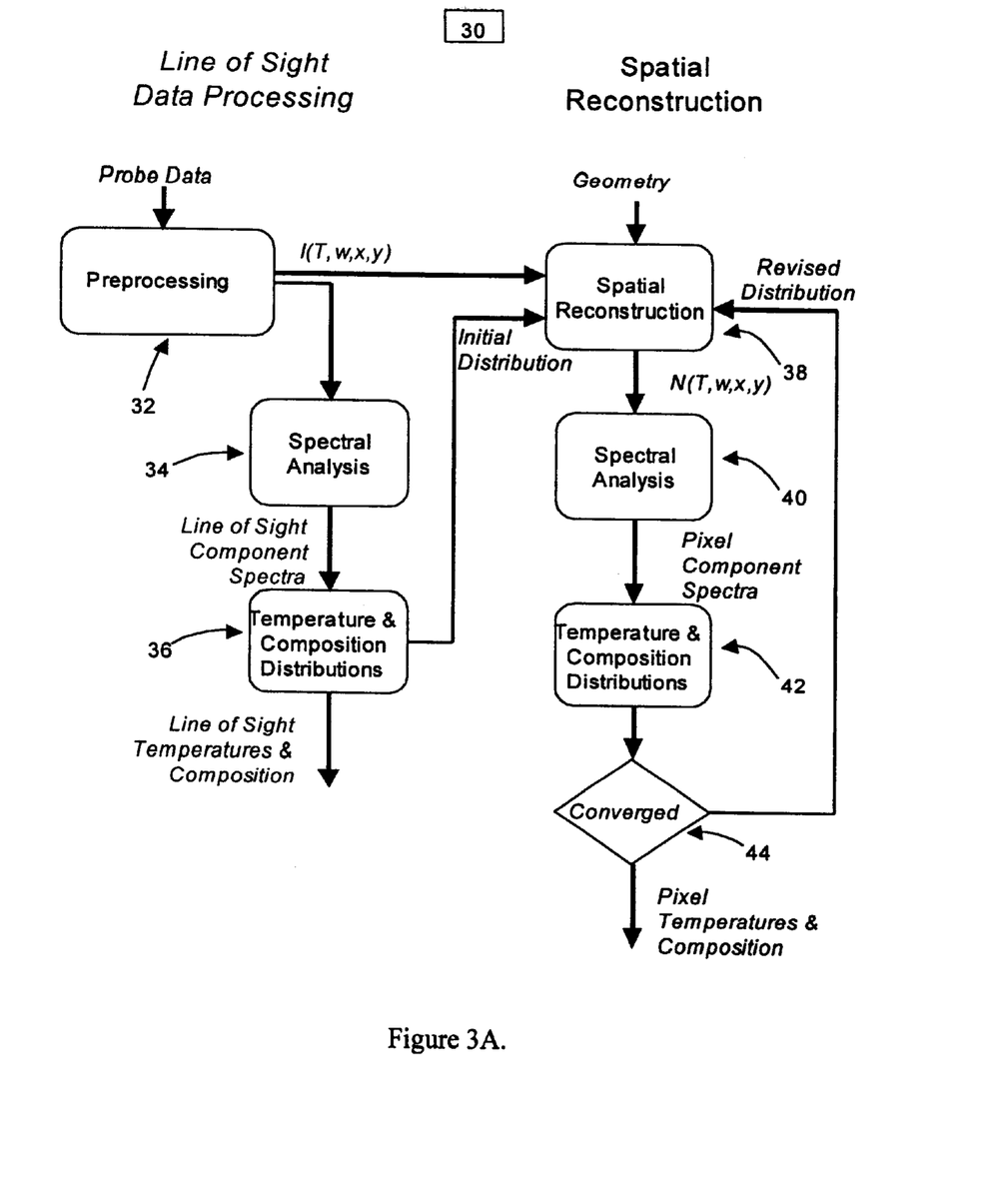
FIG. 3A is a flow chart of the overall data processing scheme for the preferred embodiment of the invention.

The measurement method of the preferred embodiment of the present invention includes collecting emitted thermal radiation, and resolving the emission spectrum over a spectral range. The resolved spectrum is then decomposed into component spectra characteristic of specific emitting species and emitter temperature. The overall data processing procedure 30 is shown in FIG. 3A. Steps 32, 34 and 36 are for determining the temperature and concentration over a line of sight through the probe field-of-view. The data is first pre-processed (step 32) to remove the instrument-specific effects and return the line of sight emission intensities, $I(T,w,x,y)$ which are a function of the temperature, T, and the wavelength, w, of the emitters, over a line of sight through the projected location x, y within the field of view. This data is subject to spectral analysis (steps 34 and 36) to determine the temperature and composition in the hot region, and then output, for example for use as control signals. Steps 38, 40, 42 and 44 outline an analogous process for determining the spatially resolved temperature and composition using tomographic reconstruction. The spatial reconstruction algorithm 38 is inserted between the preprocessing 32 and the spectral analysis 40, 42. It takes as input the line of sight emission intensities, $I(T,w,x,y)$, the probe geometry, and the average temperature output from the standard processing. The spatial reconstruction results in the emission intensity for each volume element or pixel, $x_i(T,w,x,y)$, which is then decomposed using the standard spectral analysis software to produce a set of pixel component spectra, and ultimately temperature and composition values for the pixels. The process may then be iterated (step 44) using the new pixel temperature values as input to the spatial reconstruction.

The pre-processing 32 and spectral analysis 34, 40 steps of FIG. 3A are preferably accomplished as follows. See FIG. 3B. In the preprocessing step, all instrument dependent factors are removed to yield a spectral data cube containing the emitted intensity as a function of wavelength for each fiber probe. In the next step, the spectral data cube is processed to yield temperature and species concentration information.

Figure 3B:
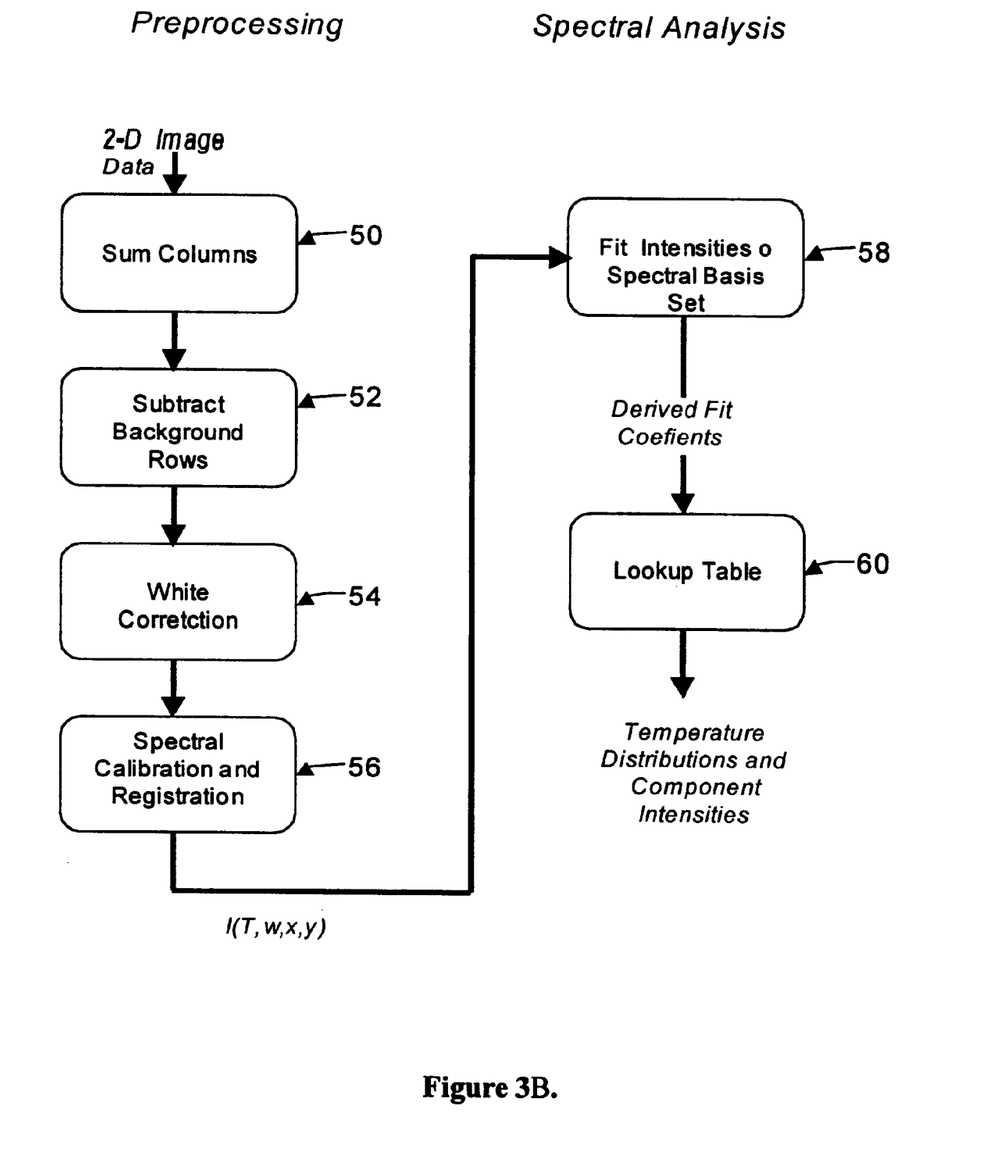
FIG. 3B is a more detailed flow chart of the pre-processing and spectral analysis steps of the process of FIG. 3A.

The preprocessing stage starts with the input data from the detector array. The input data consists of a two-dimensional image containing a series of illuminated rows corresponding to the spectrally dispersed light originating from an array of fibers at the slit entrance. Conceptually, each row of the array corresponds to a different location on the input slit. Each column of the array corresponds to a different wavelength. Using the known transfer function of the spectrograph, the data for each illuminated strip is binned by spectral element (step 50), and corrected for dark signal by comparing the illuminated sections to the non-illuminated sections (step 52). The result is an array containing the intensity observed in each column for each of the input channels. Sample data is divided by the instrument response function held in memory to yield a white-corrected spectrum in units of intensity versus column number (step 54). These data are then registered spectrally using the known spectral calibration factor for each of the data input channels (step 56). (The spectral calibration factor is different for each input channel due to geometrical factors in the spectrograph.) The data is further digitally filtered to correct for variations in spectral resolution among the various input channels in order to achieve a common spectral resolution on all channels. The result is a series of spectra with the same spectral resolution as the spectral basis functions used in the fit.

The spectral response function may be recorded once during the manufacturing process, or may be recorded periodically using an internal white light source with a known source spectral distribution function. This data is processed, corrected for the source function, and stored in memory as the instrument response function.

Spectral analysis is based on the decomposition of the spectrum into component spectra. The pre-processed spectra are fit to a library of prerecorded spectra using linear algebra techniques (step 58) and the temperature and species concentrations are determined from the fit coefficients using a calibration function contained in a lookup table (step 60). In a preferred embodiment, oblique subspace projection techniques are used to perform a least-squares sense "best fit" of the input data to the spectral library. Projection techniques are useful for real time processing, as they have a defined execution time. Typical fits such as those outlined below can be executed with processing times of the order of tens of milliseconds, allowing for analysis at video-type frame rates with standard personal computers, and potentially faster response with specialized digital signal processors. In oblique subspace projection the figure of merit for "best fit" can be adjusted to give physically meaningful results by adding physical constraints to the fit and adjusting the weight of the contribution of each wavelength element and each physical constraint to the overall error term. Physical constraints can include absolute constraints, such as requiring species concentrations to be positive, and relative constraints, such as adding to the error term for physically unreasonable results. The weight of the errors in the sum is normally adjusted to reflect the relevance of each piece of input data. For example, the spectral data is usually weighted by the inverse of the instrument noise so that the best data is given the largest weight in the sum.

The theoretical basis for the linear decomposition of spectra is as follows. The measured spectrum is an emission-weighted average of all the spectra collected from the various regions along a line-of-sight through the field of view of the probe. The emission intensity at the probe, $I_{emission}$, is given by the integrated product of the differential emissivity, $\epsilon(T, \lambda)$, and the Planck black body function, $N(T, \lambda)$, of each volume element, $dp$, along the path where $C_1$ and $C_2$ are the Planck radiation constants:

$$I_{emission} = \int_{path\ length} dp\ \epsilon(T, \lambda)\ N(T, \lambda) \quad (1)$$

$$N(T, \lambda) = C_1/\lambda^5(e^{-C_2/\lambda T} - 1) \quad (2)$$

Figure 4:
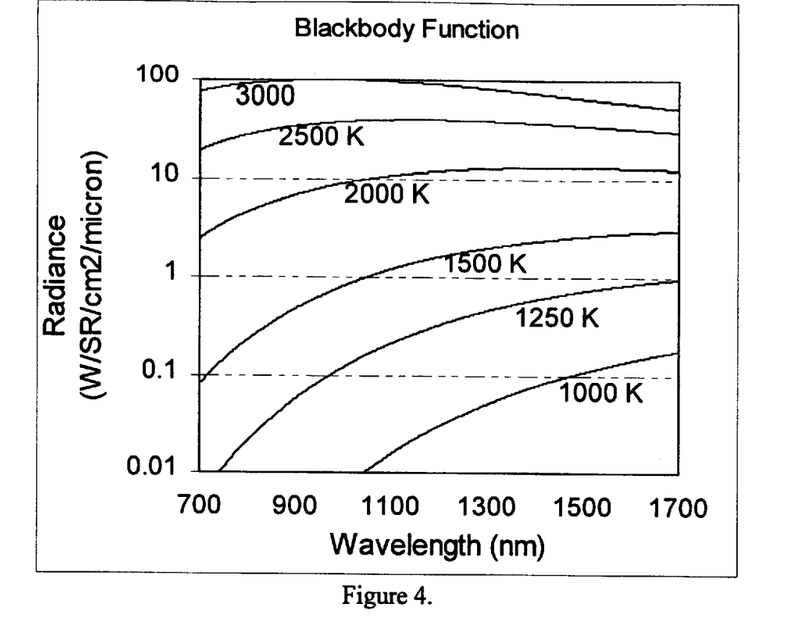
FIG. 4 illustrates the dependence of the black body function on wavelength and temperature.
Figure 5:
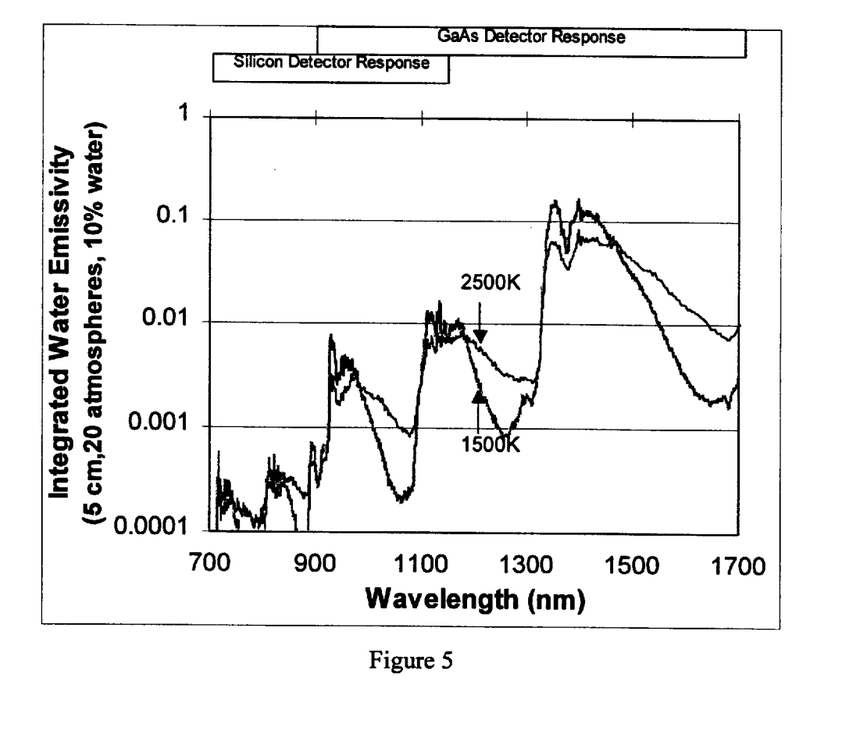
FIG. 5 illustrates the dependence of the water emissivity on wavelength for typical conditions in a turbine engine.

FIG. 4 illustrates the dependence of the black body function on wavelength and temperature. FIG. 5 illustrates the dependence of the water emissivity on wavelength for typical conditions in a turbine engine of 10% water, 4 cm path length, and pressure of 20 atmospheres.

The emissivity is defined as one minus the transmittance, t. For soot and most metal surfaces, the emissivity is uniform over a large spectral range, and independent of temperature. The soot emissivity is small for clean burning flames, and approaches unity for pure soot. Molecular emitters like water have a highly structured temperature-dependent emissivity given by Beer's law, where $k_i(\lambda, T)$ is the absorption coefficient of species i, $\rho_i$ is the number density, and l is the path length. The integrated emissivity is given by the product of the component transmittances:

$$\int_{path\ length} dp\ \epsilon(T, \lambda) = 1 - t(T, \lambda, l) = 1 - \prod_i e^{-k_i(\lambda, T)\rho_i l} \quad (3)$$

The exponential term can be approximated as a sum of linear terms, where only the first term is necessary in the optically thin limit (integrated emissivity over the line of sight much less than 1). Additional terms may be added when the integrated intensity is large.

$$\epsilon(T, \lambda) \cong \sum_i k_i(\lambda, T)\rho_i + \ldots \quad (4)$$

Each species spectrum, $k_i$ may be represented by a sum over a set of basis spectra that describe the full temperature dependence of the species spectrum. In a similar manner, the black body function can be expanded in a linear combination of terms. Thus the observed emission, which is the product of the two terms, can be linearly decomposed into a sum of temperature-dependent molecular and particulate emission spectra that are uniquely identifiable by the shape of their spectrum. The relative contributions of each basis spectrum to the species spectrum yields the temperature; the relative contributions of each species to the observed spectrum yields the relative concentration of species. The observed spectra are fit to a library containing basis spectra for all potential emitting species, such as water, soot, and other emitters for a combustor. The spectral basis library consists of a limited set of basis spectra for each species that are sufficient to fully describe the temperature dependent emission. The spectral libraries may be generated from measurements of well-characterized systems, or from the known theoretical spectrum of the species. The generation of a basis set for water is illustrated below.

Figure 6:
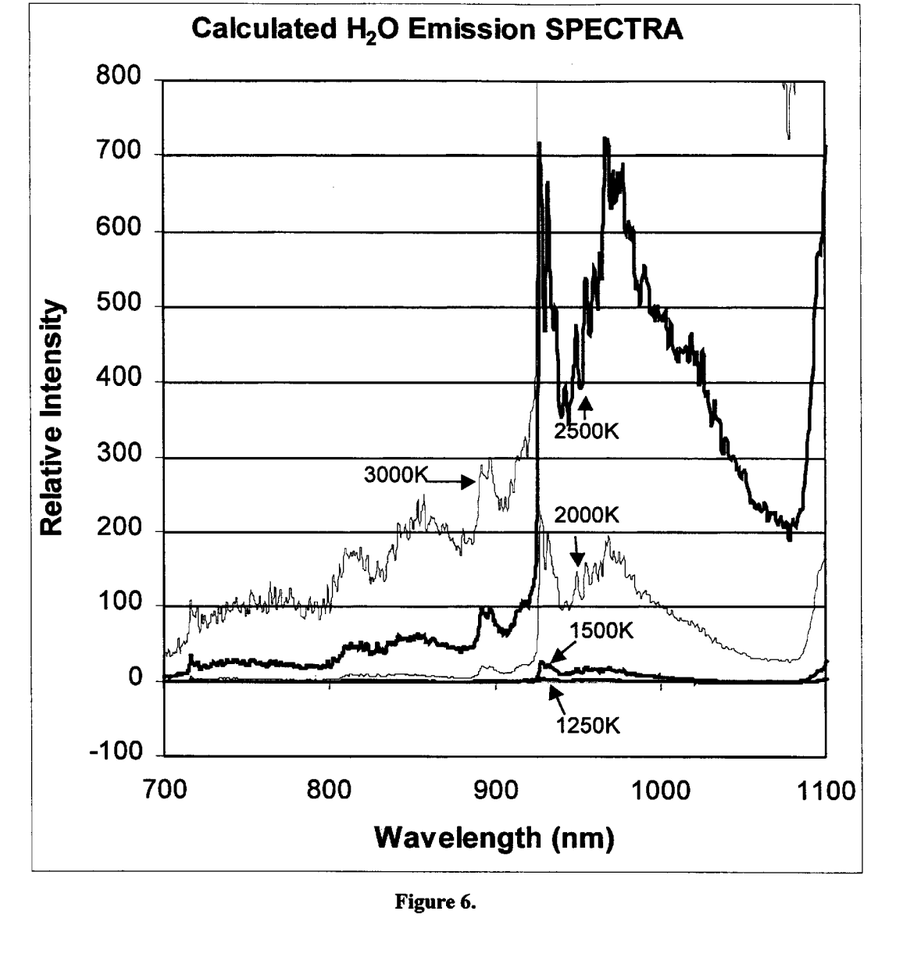
FIG. 6 shows theoretical water emission spectra at several temperatures.
Figure 7:
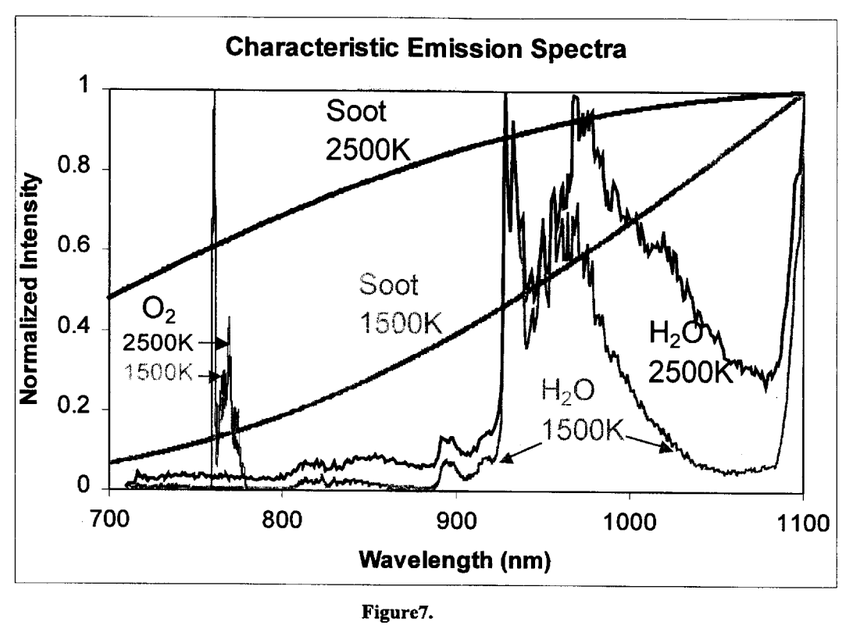
FIG. 7 shows theoretical water, soot, and $O_2$ spectra normalized to average intensity.

FIG. 6 shows theoretical water emission spectra at several temperatures. Note that the emission intensity grows rapidly with temperature, but the spectrum retains a characteristic shape. When normalized to average intensity the similarities and differences in the shape become apparent. FIG. 7 shows characteristic emission spectra for water, soot, and $O_2$ at temperatures of 1500 K and 2500 K. After removing the intensity variation with temperature, the spectral shape changes systematically with temperature and, therefore in the case of water and soot, can be used to determine the temperature of the emitting source, independent of the intensity of the emission. At this spectral resolution (2 nm FWHM), the spectral shape is completely insensitive to pressure over the full range of anticipated conditions in a turbine engine (1–40 atmospheres, 1–20 cm path length).

The full temperature range can be described with a high degree of accuracy by a small number of spectral basis functions that capture the variation of the spectrum with temperature. In one preferred implementation, basis spectra are prepared using singular value decomposition (SVD) of a set of flame emission spectra taken over a temperature range that spans the required response range of the sensor. SVD is a mathematical recasting of the data, which can allow for the reduction of basis functions necessary to represent the behavior and features of the data, thus resulting in increased computational efficiency. Alternatively, other methods, such as end member analysis, temperature derivatives, or use of pure spectra, could also be used to prepare the library spectra.

Figure 8:
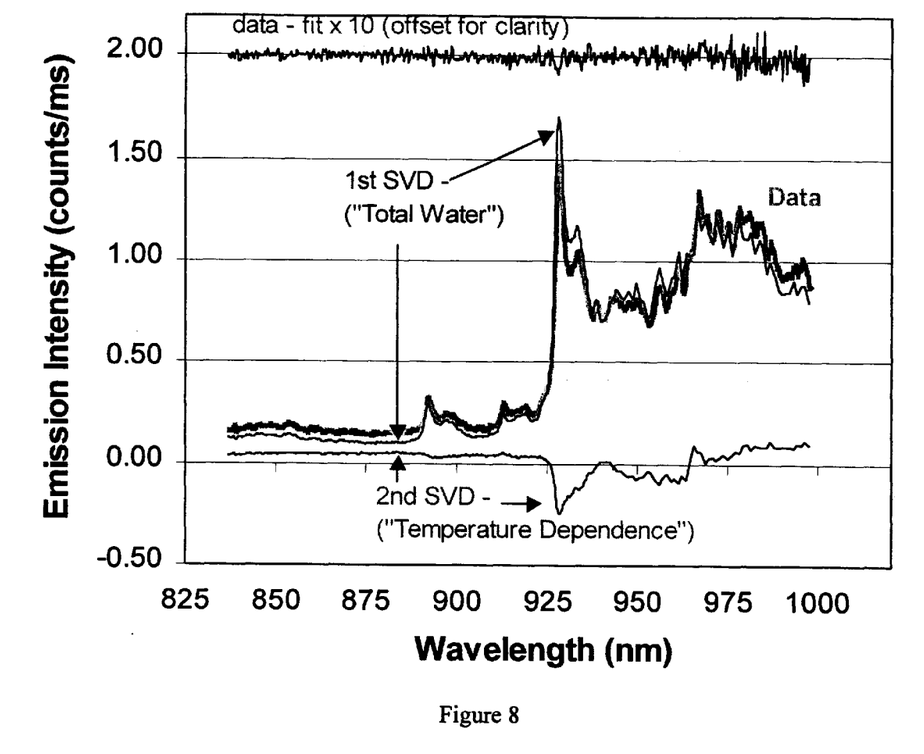
FIG. 8 illustrates a spectrum for the invention, in which only two basis functions are required to fit the temperature-dependent water spectrum.

FIG. 8 illustrates a case where only two basis functions are required to fit the temperature-dependent water spectrum. The figure shows an experimental spectrum obtained from a propane/oxygen flame (the curve labeled "data") over a small spectral range of 825–1,000 nm, and the contributions of the first ("Total Water") and second ("Temperature Dependence") spectral basis functions to the best fit The difference between the fit and the data, scaled by a factor of 10 for clarity, is shown at the top of the figure. Conceptually, the first basis function represents the intensity of the water emission, or total water concentration. It can be thought of as the average water spectrum over all represented temperatures. It describes most of the water intensity, but it does a poor job describing the temperature-dependent details of the spectrum. A substantial amount of the second basis function is combined with the first function to yield the "best fit" to the observed data. The second basis function represents the temperature dependence of the water spectral shape. In the case of FIG. 8, the water emission is hotter than average, and the second basis function removes intentsity from the peak and adds intensity at the wings of the bands. Note that even though the second basis function makes negative contributions to the intensity at some wavelengths, the total water intensity obtained from the sum of the two basis functions is constrained to always be positive. The ratio of the coefficients of the first two basis functions is a function of the temperature and can be converted to the true temperature using a calibration function. Based on a calibration function determined from thermocouple measurements, the derived temperature for the spectrum in FIG. 8 is 2480 K (4000 F). No measurable soot was detected in the flame spectrum.

Figure 9:
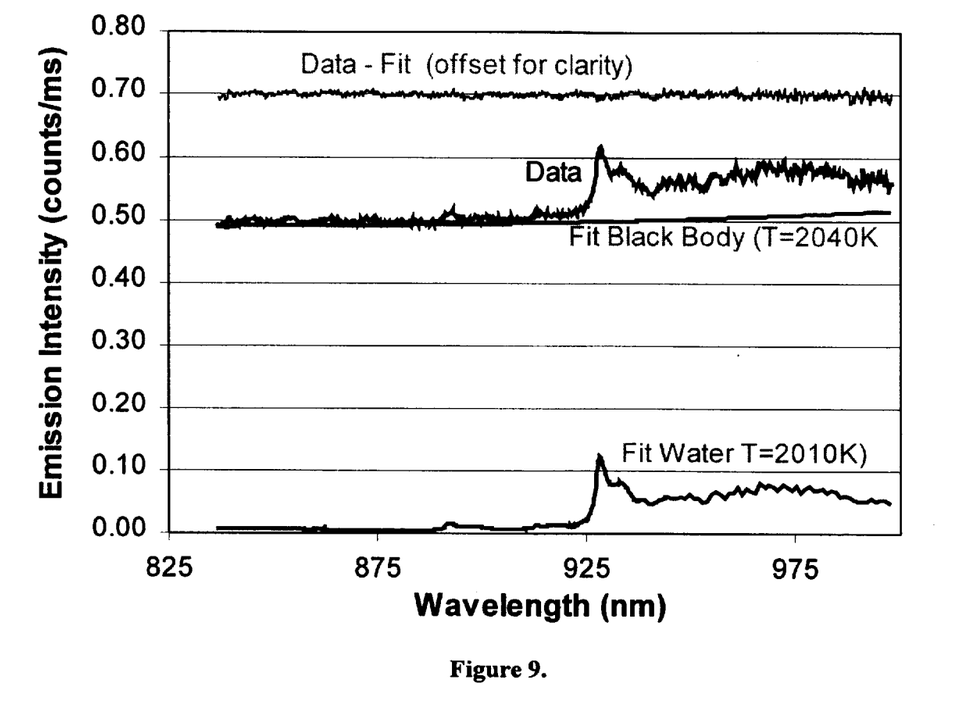
FIG. 9 demonstrates the decomposition of a spectrum into soot and water components.

FIG. 9 demonstrates the decomposition of a spectrum into soot and water components. The data line shows a spectrum collected from the active combustion region of a high-pressure, high-temperature, liquid-fuel combustor cell, using a fiber probe. The observed spectrum consists of structured water emission features (lower curve) riding on top of a large thermal emission continuum (the Black Body curve). The thermal emission arises from hot soot in the flow, and from the chamber walls in the field-of-view of the probe. Oblique subspace projection at was used to decompose the spectrum into the black body and water emissions. Two basis spectra were used to describe the water spectrum, and four basis spectra were used to describe the soot. For this measurement, the derived soot temperature is 2040 K, while the water temperature was determined to be 2010 K. The integrated intensities of the soot and water emissions are directly related to species concentrations. The intensity of the soot was seen to vary strongly and continuously with fuel inlet conditions, increasing by as much as a factor of two when resonant instabilities were induced in the combustor, and thus could be used to control the fuel flow rate to achieve a minimum soot operating condition.

In each preferred embodiment, the spectral region and measurement geometry is selected to emphasize the properties to be measured. Wavelengths are selected based on the molecules of interest, the temperature of the hot region, and the type of temperature information that is desired. The selection of wavelength range is governed by equations 1–4. It is convenient to select measurement locations and spectral regions where the integrated emissivity over the path length is less than one. This optically thin limit is met for soot at many locations in the burner, including at the exit of the combustion region. Ideally, the spectral region is chosen so that the molecular emissions are optically thin, but are large enough to be detected in the presence of soot emission. Under the conditions shown in FIG. 5, water is optically thin for all wavelengths below 2000 nm.

Details of the temperature distribution along the line-of-sight can be distinguished by separating the effects of the spectral band shape from the black body emission function. An observed spectrum is actually a weighted composite of curves from all temperature regions in the instrument line-of-sight. Because of the large temperature-dependence of the blackbody emission intensity, the signal is strongly weighted towards the hot regions. The probe can therefore be placed well away from the hot region and see little or no interference from the be intervening cold regions. Data collected over a large wavelength range yield further details of the temperature distributions along the line of sight. Emission at the shortest wavelengths arises predominately from the hottest regions in the line-of-sight. Conversely, cooler regions make a larger relative contribution to emissions at the longest wavelengths. As a result, temperatures extracted from the short wavelength side of the thermal emission are representative of the hottest emitters in the sensor field-of-view, and temperatures from the long wavelength side are more strongly influenced by the cooler temperature regions.

In a preferred embodiment for turbine engine temperature measurements, a silicon detector operating within a range of 700–1200 nm could be used, in order to take advantage of the large temperature dependence of the black body function in this wavelength range. Water emissivities are of the order of 0.1 to 1 percent in this range, and have a strong dependence on temperature.

For an alternative embodiment designed for lower temperatures or lower water densities, the spectral range of 100–1700 nm might be used to take advantage of the larger emission intensity and water emissivity at these wavelengths.

Figure 10A:
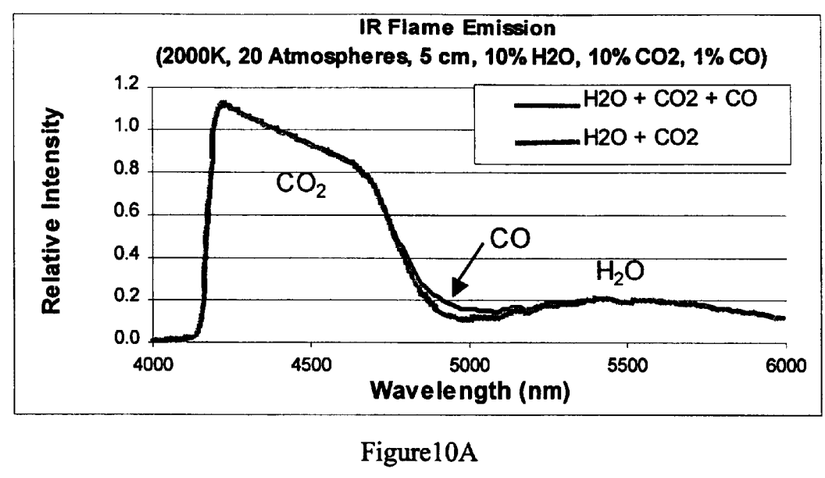
FIG. 10A shows the predicted spectrum with and without CO for a representative case.
Figure 10B:
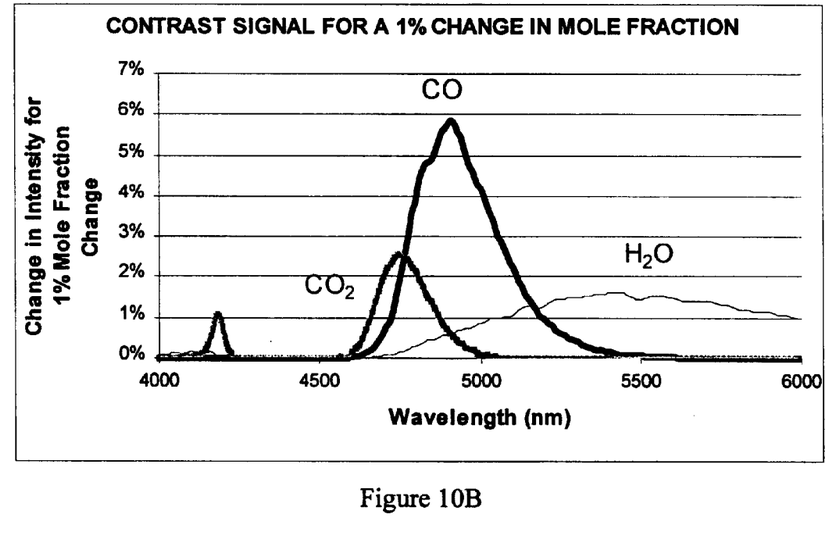
FIG. 10B shows the change in the spectrum of FIG. 10A associated with changes in CO, $CO_2$, and $H_2O$ concentrations.

In an alternative embodiment designed for detecting CO, $CO_2$ and water at the turbine blade entrance, measurements might be made in the infrared region centered on the CO fundamental absorption around 5 microns as shown in FIG. 10. FIG. 10A shows the predicted spectrum with and without CO for a representative case. FIG. 10B shows the change in the spectrum associated with changes in CO, $CO_2$, and $H_2O$ concentrations. The CO band overlaps $H_2O$ and $CO_2$ bands. The $CO_2$ band is black in the center, but has a low emissivity at the edges. The CO and water are optically thin. The CO can be detected in the trough between the water and $CO_2$ bands. As each band has a unique shape, the observed spectrum can be decomposed into component spectra to determine the relative concentrations of CO, $CO_2$, and $H_2O$.

What is claimed is:

1. A system for remotely determining at least one of the temperature of, and the relative concentrations of species making up, a hot fluid, based on the spectral structure of radiation emitted from the fluid, comprising:
   at least one passive optical probe for collecting emitted thermal radiation over a field of view including the hot fluid;
   a spectrograph for resolving at least a portion of the emission spectrum from the collected radiation;
   means for decomposing the resolved emission spectrum into a combination of basis spectra that are characteristic of specific emitting species and emitter temperatures in the hot fluid, by fitting the emission spectrum to at least two basis spectra for each species, one basis spectrum incorporating temperature dependent aspects of the emissivity spectrum of that species, and one basis spectrum incorporating temperature-independent aspects of the emissivity spectrum of that species; and
   means for determining, from the relative amounts of at least two spectra, at least one of the temperature of, and the relative concentrations of species making up, the hot fluid.

2. A method of remotely determining at least one of the temperature of, and the relative concentrations of species making up, a hot fluid, based on the spectral structure of radiation emitted from the fluid, comprising:
   collecting emitted thermal radiation over a field of view including the hot fluid;
   resolving, using a spectrograph, at least a portion of the emission spectrum from the collected radiation;
   decomposing the resolved emission spectrum into a combination of basis spectra that are characteristic of specific emitting species and emitter temperatures; and
   determining, from the relative amounts of at least two basis spectra, at least one of the temperature of, and the relative concentrations of species making up, the hot fluid.

3. A method of remotely determining at least one of the temperature of, and the relative concentrations of species making up, a hot fluid, based on the spectral structure of radiation emitted from the fluid, comprising:
   collecting emitted thermal radiation over a field of view including the hot fluid;
   resolving the emission spectrum in the infrared spectral range of 1.5–13 microns from the collected radiation;
   decomposing the resolved emission spectrum into a combination of basis spectra that are characteristic of specific emitting species and emitter temperatures; and
   determining, from the relative amounts of at least two basis spectra, at least one of the temperature of, and the relative concentrations of species making up, the hot fluid.

4. A method of remotely determining at least one of the temperature of, and the relative concentrations of species making up, a hot fluid, based on the spectral structure of radiation emitted from the fluid, comprising:
   collecting emitted thermal radiation over a field of view including the hot fluid;
   resolving at least a portion of the emission spectrum from the collected radiation;
   decomposing the resolved emission spectrum into a combination of basis spectra that are characteristic of specific emitting species and emitter temperatures; and
   determining, by comparing the relative amounts of basis spectra for at least two different species to determine the concentrations, the relative concentrations of species making up, the hot fluid.

5. The method of claim 4 wherein the basis spectra are predetermined based on the known emissivity spectrum of each species and the Planck black body function.

6. A method of remotely determining at least one of the temperature of, and the relative concentrations of species making up, a hot fluid, based on the spectral structure of radiation emitted from the fluid, comprising:
   collecting emitted thermal radiation over a field of view including the hot fluid;
   resolving at least a portion of the emission spectrum from the collected radiation;
   decomposing the resolved emission spectrum into a combination of basis spectra that are characteristic of specific emitting species and emitter temperatures, wherein the basis spectra are predetermined based on the known emissivity spectrum of each species and the Planck black body function, and wherein the basis spectra are normalized to remove the wavelength independent aspects of the emission intensity but retain the characteristic spectral shape; and
   determining, from the relative amounts of at least two basis spectra, at least one of the temperature of, and the relative concentrations of species making up, the hot fluid.

7. The method of claim 6 wherein the determining step comprises comparing the relative amounts of basis spectra for the same species to determine the temperature.

8. A method of remotely determining at least one of the temperature of, and the relative concentrations of species making up, a hot fluid, based on the spectral structure of radiation emitted from the fluid, comprising:
   collecting emitted thermal radiation over a field of view including the hot fluid;
   resolving the emission spectrum in the range of 600–1700 nm from the collected radiation;
   decomposing the resolved emission spectrum into a combination of basis spectra that are characteristic of specific emitting species and emitter temperatures; and
   determining, from the relative amounts of at least two basis spectra, at least one of the temperature of, and the relative concentrations of species making up, the hot fluid.

9. The method of claim 8 wherein the decomposing step comprises fitting the emission spectrum to a linear combination of at least two basis spectra.

10. The method of claim 9 wherein the decomposing step comprises oblique subspace projection.

11. The method of claim 8 wherein the hot fluid is in a combustor.

12. The method of claim 11 wherein the combustor is in a turbine engine.

13. A method of remotely determining at least one of the temperature of, and the relative concentrations of species making up, a hot fluid, based on the spectral structure of radiation emitted from the fluid, comprising:
   collecting emitted thermal radiation over a field of view including the hot fluid;
   resolving at least a portion of the emission spectrum from the collected radiation;

decomposing the resolved emission spectrum into a combination of basis spectra that are characteristic of specific emitting species and emitter temperatures;

determining, from the relative amounts of at least two basis spectra, at least one of the temperature of, and the relative concentrations of species making up, the hot fluid; and using at least one of the determined temperature and species make-up to control one or more inputs to the hot fluid.

14. The method of claim 13 wherein the collecting step comprises the use of a passive optical probe.

15. The method of claim 14 wherein the collecting step further comprises the use of fiber optics to carry collected radiation.

16. The method of claim 13 wherein one basis spectrum incorporates linear temperature dependent aspects of the emissivity spectrum, and one basis spectrum incorporates temperature-independent aspects of the emissivity spectrum.

17. The method of claim 13 wherein the hot fluid is in a turbine engine.

18. The method of claim 13 wherein the hot fluid results from combustion, and the controlled input is the fuel/oxidizer ratio.

19. A method of remotely determining at least one of the temperature of, and the relative concentrations of species making up, a hot fluid, based on the spectral structure of radiation emitted from the fluid, comprising:

collecting emitted thermal radiation over a plurality of fields of view including the hot fluid to determine a spatial profile of the hot fluid;

resolving at least a portion of the emission spectrum from the collected radiation;

decomposing the resolved emission spectrum into a combination of basis spectra that are characteristic of specific emitting species and emitter temperatures; and determining, from the relative amounts of at least two basis spectra, at least one of the temperature of, and the relative concentrations of species making up, the hot fluid.

20. The method of claim 19 wherein the basis spectra comprise temperature-dependent spectral signatures for at least one species.

21. The method of claim 19 wherein the hot fluid is in a turbine engine defining an annulus, and the plurality of fields of view are spaced radially around the turbine engine annulus, to determine a radial profile of hot fluid in the turbine engine.

22. The method of claim 19 wherein the hot fluid includes one or more species within the group of species consisting of water, oxygen, soot, carbon dioxide, and carbon monoxide.

23. The method of claim 19 wherein the collecting step comprises collecting radiation simultaneously over a plurality of overlapping fields of view that each define a volume element.

24. The method of claim 23 wherein the resolving step comprises resolving the emission spectra from each of the volume elements defined by the overlapping fields of view.

25. The method of claim 23 wherein the determining step comprises determining the spatially-resolved temperature profile of the hot fluid.

26. The method of claim 23 wherein the determining step comprises determining the spatially-resolved composition profile of the hot fluid.

27. A system for remotely determining at least one of the temperature of, and the relative concentrations of species making up, a hot fluid, based on the spectral structure of radiation emitted from the fluid, comprising:

at least one passive optical probe for collecting emitted thermal radiation over a field of view including the hot fluid;

an instrument for resolving at least a portion of the emission spectrum from the collected radiation;

means for decomposing the resolved emission spectrum into a combination of basis spectra that are characteristic of specific emitting species and emitter temperatures, wherein the basis spectra are predetermined based on the known emissivity spectrum of each species and the Planck black body function, and wherein the basis spectra are normalized to remove the wavelength independent aspects of the emission intensity but retain the characteristic spectral shape; and means for determining, from the relative amounts of at least two basis spectra, at least one of the temperature of, and the relative concentrations of species making up, the hot fluid.

28. A system for remotely determining at least one of the temperature of, and the relative concentrations of species making up, a hot fluid, based on the spectral structure of radiation emitted from the fluid, comprising:

at least one passive optical probe for collecting emitted thermal radiation over a field of view including the hot fluid;

an instrument for resolving at least a portion of the emission spectrum from the collected radiation;

means for decomposing the resolved emission spectrum into a combination of basis spectra that are characteristic of specific emitting species and emitter temperatures; and means for determining, from the relative amounts of at least two basis spectra, at least one of the temperature of, and the relative concentrations of species making up, the hot fluid, wherein the means for determining relative concentrations comprises means for comparing the relative amounts of basis spectra for at least two different species.

29. A system for remotely determining at least one of the temperature of, and the relative concentrations of species making up, a hot fluid, based on the spectral structure of radiation emitted from the fluid, comprising:

at least one passive optical probe for collecting emitted thermal radiation over a field of view including the hot fluid;

a spectrograph for resolving at least a portion of the emission spectrum from the collected radiation;

means for decomposing the resolved emission spectrum into a combination of basis spectra that are characteristic of specific emitting species and emitter temperatures; and means for determining, from the relative amounts of at least two basis spectra, at least one of the temperature of, and the relative concentrations of species making up, the hot fluid.

30. A system for remotely determining at least one of the temperature of, and the relative concentrations of species making up, a hot fluid, based on the spectral structure of radiation emitted from the fluid, comprising:

at least one passive optical probe for collecting emitted thermal radiation over a field of view including the hot fluid;

an instrument for resolving the emission spectrum in the infrared spectral range of 1.5–13 microns from the collected radiation;

means for decomposing the resolved emission spectrum into a combination of basis spectra that are characteristic of specific emitting species and emitter temperatures; and means for determining, from the relative amounts of at least two basis spectra, at least one of the temperature of, and the relative concentrations of species making up, the hot fluid.

31. The system of claim 30 wherein the hot fluid includes one or more species within the group of species consisting of water, oxygen, soot, carbon dioxide, and carbon monoxide.

32. A system for remotely determining at least one of the temperature of, and the relative concentrations of species making up, a hot fluid, based on the spectral structure of radiation emitted from the fluid, comprising:

at least one passive optical probe for collecting emitted thermal radiation over a field of view including the hot fluid;

an instrument for resolving the emission spectrum in the range of 600–1700 nm from the collected radiation;

means for decomposing the resolved emission spectrum into a combination of basis spectra that are characteristic of specific emitting species and emitter temperatures; and means for determining, from the relative amounts of at least two basis spectra, at least one of the temperature of, and the relative concentrations of species making up, the hot fluid.

33. The system of claim 32 wherein the hot fluid is in a combustor.

34. The system of claim 32 wherein the combustor is in a turbine engine.

35. The system of claim 29 wherein the means for decomposing comprises means for fitting the emission spectra to a linear combination at least two basis spectra.

36. The system of claim 35 wherein the means for fitting comprises means for accomplishing an oblique subspace projection.

37. A system for remotely determining at least one of the temperature of, and the relative concentrations of species making up, a hot fluid, based on the spectral structure of radiation emitted from the fluid, comprising:

at least one passive optical probe for collecting emitted thermal radiation over a field of view including the hot fluid;

an instrument for resolving at least a portion of the emission spectrum from the collected radiation;

means for decomposing the resolved emission spectrum into a combination of basis spectra that are characteristic of specific emitting species and emitter temperatures;

means for determining, from the relative amounts of at least two basis spectra, at least one of the temperature of, and the relative concentrations of species making up, the hot fluid; and means, responsive to at least one of the determined temperature and species make-up, for controlling one or more inputs to the hot fluid.

38. The system of claim 37 further comprising fiber optics to carry collected radiation from the at least one probe to the instrument.

39. The system of claim 37 wherein the basis spectra are predetermined based on the known emissivity spectrum of each species and the Planck black body function.

40. The system of claim 37 wherein one basis spectrum incorporates linear temperature dependent aspects of the emissivity spectrum, and one basis spectrum incorporates temperature-independent aspects of the emissivity spectrum.

41. The system of claim 37 wherein the means for determining temperature comprises means for comparing relative amounts of at least two basis spectra for the same species.

42. The system of claim 37 wherein the hot fluid is in a turbine engine.

43. The system of claim 37 wherein the hot fluid results from combustion, and the controlled input is the fuel/oxidizer ratio.

44. A system for remotely determining at least one of the temperature of, and the relative concentrations of species making up, a hot fluid, based on the spectral structure of radiation emitted from the fluid, comprising:

a plurality of passive optical probes each of which collects emitted thermal radiation from at least one field of view including the hot fluid, to determine a spatial profile of the hot fluid;

an instrument for resolving at least a portion of the emission spectrum from the collected radiation;

means for decomposing the resolved emission spectrum into a combination of basis spectra that are characteristic of specific emitting species and emitter temperatures; and means for determining, from the relative amounts of at least two basis spectra, at least one of the temperature of, and the relative concentrations of species making up, the hot fluid.

45. The system of claim 44 wherein the basis spectra comprise temperature-dependent emissivity spectra for at least one species.

46. The system of claim 44 wherein the hot fluid is in a turbine engine defining an annulus, and the plurality of optical probes are spaced radially around the turbine engine annulus, to determine a radial profile of hot fluid in the turbine engine.

47. The system of claim 44 wherein the means for collecting comprises means for collecting radiation simultaneously over a plurality of overlapping fields of view that each define a volume element.

48. The system of claim 47 wherein the means for resolving comprises means for resolving the emission spectra from each of the volume elements defined by the overlapping fields of view.

49. The system of claim 47 wherein the means for determining comprises means for determining the spatially-resolved temperature profile of the hot fluid.

50. The system of claim 47 wherein the means for determining comprises means for determining the spatially-resolved composition profile of the hot fluid.

* * * * *